(12) United States Patent
Shioiri

(10) Patent No.: US 10,350,715 B2
(45) Date of Patent: Jul. 16, 2019

(54) METHOD OF PRODUCING A MEDICAL CUTTING INSTRUMENT

(71) Applicant: Mutsunori Shioiri, Utsunomiya (JP)

(72) Inventor: Mutsunori Shioiri, Utsunomiya (JP)

(73) Assignee: MANI , INC., Utsunomiya-Shi, Tochigi (JP)

(*) Notice: Subject to any disclaimer, the term of this patent is extended or adjusted under 35 U.S.C. 154(b) by 56 days.

(21) Appl. No.: 15/363,703

(22) Filed: Nov. 29, 2016

(65) Prior Publication Data
US 2017/0072519 A1 Mar. 16, 2017

Related U.S. Application Data

(62) Division of application No. 13/807,659, filed as application No. PCT/JP2011/064689 on Jun. 27, 2011.

(30) Foreign Application Priority Data

Jun. 30, 2010 (JP) .................................. 2010-149498

(51) Int. Cl.
  *B23P 15/28* (2006.01)
  *B23K 1/00* (2006.01)
  (Continued)

(52) U.S. Cl.
  CPC ............... *B23P 15/28* (2013.01); *A61C 1/00* (2013.01); *A61C 3/02* (2013.01); *B23K 1/0008* (2013.01);
  (Continued)

(58) Field of Classification Search
  CPC .. A61C 3/02; A61C 1/00; B23P 15/28; B23K 1/0008; B23K 1/19; B23K 2201/20; B23K 2203/05; B23K 2203/52; B23K 2203/18
  (Continued)

(56) References Cited

U.S. PATENT DOCUMENTS

| 965,587 A | 7/1910 | Lassiter ................. B23B 27/18 219/137 R |
| 1,885,679 A | 11/1932 | Brooks .................. B23B 27/18 407/118 |

(Continued)

FOREIGN PATENT DOCUMENTS

| EP | 2 589 353 A1 * | 5/2013 |
| JP | 49-123270 | * 11/1974 |

(Continued)

OTHER PUBLICATIONS

Translation of JP 49-123270 to Hitachi et al, published 1974.
Translation of WO 2009/107595 retrieved on Apr. 8, 2014.

*Primary Examiner* — Hwei-Siu C Payer
(74) *Attorney, Agent, or Firm* — Shlesinger, Arkwright & Garvey LLP

(57) ABSTRACT

A method of producing a medical cutting instrument. Medical cutting instrument is provided which stably exhibits high joint strength obtained by brazing. Cutting instrument is configured by providing a working section to a front end of a shank section. Working section consists of a carbide or a ceramic, shank section being constructed from round stainless steel bar or round tool steel bar. Shank section and working section are connected through a brazed section. Brazed section is portion at which shank section and working section are brazed together while brazing surfaces, which are provided with protrusion sections formed on shank section and/or working section, are caused to be in contact with each other. Protrusion sections each have sloped surfaces having an apex, and the height of the sloped surfaces is set in range of 0.5%-8%, inclusive, of the diameter of the brazing surface of the shank section.

2 Claims, 3 Drawing Sheets

(51) Int. Cl.
  *B23K 1/19* (2006.01)
  *A61C 3/02* (2006.01)
  *A61C 1/00* (2006.01)
  *B23K 101/20* (2006.01)
  *B23K 103/04* (2006.01)
  *B23K 103/18* (2006.01)
  *B23K 103/00* (2006.01)

(52) U.S. Cl.
  CPC ............ *B23K 1/19* (2013.01); *B23K 2101/20* (2018.08); *B23K 2103/05* (2018.08); *B23K 2103/18* (2018.08); *B23K 2103/52* (2018.08)

(58) Field of Classification Search
  USPC .......................................................... 76/115
  See application file for complete search history.

(56) References Cited

U.S. PATENT DOCUMENTS

| | | | | |
|---|---|---|---|---|
| 2,334,755 A * | 11/1943 | Eglinton | ............... | A61C 3/02 |
| | | | | 228/245 |
| 2,336,297 A | 12/1943 | Rooke | ............... | 285/288.1 |
| 2,575,332 A | 11/1951 | Cummins | ............... | 408/144 |
| 2,708,853 A | 5/1955 | MacLean | ............... | 408/226 |
| 2,748,483 A | 6/1956 | Hoffmeister | ............... | 433/166 |
| 3,670,416 A | 6/1972 | Kroder | ............... | A61C 3/02 |
| | | | | 408/226 |
| 4,008,976 A | 2/1977 | Holzl | ............... | B21D 37/205 |
| | | | | 407/119 |
| 5,112,165 A | 5/1992 | Hedlund | ............... | B28D 1/188 |
| | | | | 299/106 |
| 5,213,452 A * | 5/1993 | Kirby | ............... | B23C 5/1081 |
| | | | | 407/118 |
| 5,816,807 A * | 10/1998 | Matsutani | ............... | A61C 3/02 |
| | | | | 433/165 |
| 5,845,547 A | 12/1998 | Sollami | ............... | E21C 35/183 |
| | | | | 175/420.1 |
| 6,164,916 A | 12/2000 | Frost et al. | ............... | 416/189 |
| 6,315,065 B1 | 11/2001 | Yong | ............... | E21B 10/573 |
| | | | | 175/426 |
| 6,508,318 B1 * | 1/2003 | Linden | ............... | E21B 10/56 |
| | | | | 175/414 |
| 6,676,410 B2 | 1/2004 | Beppu | ............... | 433/166 |
| 8,783,389 B2 | 7/2014 | Fan | ............... | B24D 99/005 |
| | | | | 175/433 |
| 2006/0157285 A1 | 7/2006 | Cannon | ............... | E21B 10/36 |
| | | | | 175/374 |
| 2009/0117517 A1* | 5/2009 | Koster | ............... | A61C 3/02 |
| | | | | 433/166 |
| 2009/0170053 A1 | 7/2009 | Ikemi | ............... | 433/166 |
| 2010/0190423 A1 | 7/2010 | Sung | ............... | 451/443 |
| 2010/0206641 A1 | 8/2010 | Hall | ............... | E21B 10/55 |
| | | | | 175/426 |
| 2011/0031036 A1 | 2/2011 | Patel | ............... | E21B 10/5673 |
| | | | | 175/430 |
| 2011/0120782 A1 | 5/2011 | Cooley | ............... | B24D 99/005 |
| | | | | 175/432 |
| 2011/0195377 A1* | 8/2011 | Sun | ............... | A61C 3/02 |
| | | | | 433/165 |
| 2012/0247834 A1 | 10/2012 | Buxbaum | ............... | E21B 10/5673 |
| | | | | 175/57 |
| 2013/0068539 A1 | 3/2013 | Vempati | ............... | E21B 10/5735 |
| | | | | 175/434 |
| 2013/0122461 A1* | 5/2013 | Shioiri | ............... | A61B 17/16 |
| | | | | 433/144 |
| 2013/0171583 A1* | 7/2013 | Shioiri | ............... | A61C 3/02 |
| | | | | 433/144 |
| 2017/0072519 A1* | 3/2017 | Shioiri | ............... | A61C 3/02 |

FOREIGN PATENT DOCUMENTS

| | | | | |
|---|---|---|---|---|
| JP | 52050906 A | 4/1977 | ............ | B23B 27/00 |
| JP | 62-150012 U1 | 9/1987 | | |
| JP | 63-041409 U1 | 3/1988 | | |
| WO | WO2009/107595 | 3/2009 | | |
| WO | 2009/107595 A1 | 9/2009 | | |
| WO | WO 2012/014979 A1 * | 2/2012 | | |

\* cited by examiner (a)

(b)

(c)

METHOD OF PRODUCING A MEDICAL CUTTING INSTRUMENT

TECHNICAL FIELD

The present invention relates to a medical cutting instrument which is used to cut a surface layer of a tooth, a bone including an alveolar bone, and the like used during dental treatment.

BACKGROUND

For example, in dental treatment, a desired treatment may be performed by cutting a surface layer of a tooth. A medical cutting instrument used during the treatment includes a shank portion gripped by a chuck of a handpiece, and a working portion continuously formed of the shank portion and including a cutting blade which is used to cut a surface layer from an outer circumference to a leading end portion. When a doctor presses a portion to be treated with the working portion while rotating the medical cutting instrument by operating the handpiece, the desired treatment is performed by cutting the surface layer.

In the medical cutting instrument with the above-described configuration, cemented carbide represented by tungsten carbide is generally used for the working portion to ensure a cutting performance with respect to a hard surface layer. However, when the shank portion is also formed using cemented carbide, a problem of increasing the number of hours for processing occurs.

Thus, as the medical cutting instrument, an instrument in which a shank portion is formed of stainless steel or tool steel, and cemented carbide forming a working portion is connected to a front end of the shank portion through butt-jointing is provided. In this way, when different metals such as stainless steel or tool steel and cemented carbide are bonded to each other, a method such as friction pressure welding, resistance welding, or brazing is selectively employed in general.

SUMMARY OF INVENTION

Technical Problem

In a medical cutting instrument provided by welding stainless steel or tool steel forming a shank portion and cemented carbide forming a working portion using friction pressure welding or resistance welding, there are problems in that a variation occurs in a joint strength in a bonding surface and a fraction defective increases.

In addition, in a medical cutting instrument provided by brazing stainless steel or tool steel forming a shank portion and cemented carbide forming a working portion, bonding surfaces of the shank portion and the working portion are formed as a flat surface, and the bonding surfaces come into contact with each other and are brazed. In a case of such a medical cutting instrument, there occurs a problem that a joint strength varies in response to a variation of a gap between the bonding surfaces.

An object of the invention is to provide a medical cutting instrument capable of stably exhibiting a high joint strength.

Solution to Problem

To resolve the above problem, a medical cutting instrument according to the invention is a medical cutting instrument provided with a working portion formed of cemented carbide or ceramic at a leading end of a shank portion formed by a round stainless steel bar or a round tool steel bar, wherein stainless steel or tool steel forming the shank portion and cemented carbide or ceramic forming the working portion are bonded to each other through a brazing portion, the brazing portion being brazed while brazing surfaces, which are provided with protrusion portions formed on one or both of the shank portion and the working portion, are caused to be in contact with each other.

In the medical cutting instrument, it is preferable that the protrusion portion provided on the brazing surface be formed as a sloped surface including an apex, and brazing be performed while the apex is in contact with a flat surface or a sloped surface including an apex in a sloped surface including an apex provided on an opposing brazing surface, and it is preferable that the sloped surface including the apex be formed on a brazing surface formed at an edge in an axial direction of the round stainless steel bar or the round tool steel bar forming the shank surface, and a height of the sloped surface be set in a range of 0.5% to 8% of a diameter of the brazing surface of stainless steel or tool steel.

Advantageous Effects of Invention

In a medical cutting instrument according to the invention, a protrusion portion is provided on one or both of a brazing surface formed at an edge of a shank portion and a brazing surface formed at an edge of a working portion, and brazing is performed while the brazing surfaces face and come into contact with each other. That is, since the brazing surface of the shank portion and the brazing surface of the working portion face and come into contact with each other, a portion of an exterior surface forming a protrusion portion provided on one brazing surface comes into contact with a portion of an exterior surface forming a protrusion portion provided on the other surface or a portion of a surface formed in a shape different from a protrusion portion.

Thus, a void corresponding to a shape of protrusion portions or a void corresponding to a shape of a protrusion portion and a shape different from a protrusion portion is formed between the brazing surfaces which come into contact with each other. A gap of the voids does not change since the both brazing surfaces come into contact with each other. Accordingly, during brazing, a volume of a void where a solder is filled is constant, and a stable brazing operation without a variation can be performed. As a result, it is possible to stably exhibit a high joint strength.

In particular, when a protrusion portion provided on a brazing surface is formed as a sloped surface including an apex, and the apex comes into contact with a flat surface or a sloped surface including an apex in a sloped surface including an apex provided on an opposing brazing surface, a contact area is substantially a point contact. Thus, a void formed between the opposing brazing surfaces has a shape in which a gap decreases toward the apex. Accordingly, the void exhibits capillary phenomenon. When a solder filled in the void is melted, the solder is attracted toward the apex and is inhibited from flowing to the outside. Thus, a stable brazing operation can be performed.

Further, when the height of the sloped surface is in the range of 0.5% to 8% of the diameter of the brazing surface, the distance between the opposing brazing surfaces can be decreased, and the capillary phenomenon can be stably exhibited.

REFERENCE SIGNS LIST

Figure 1:
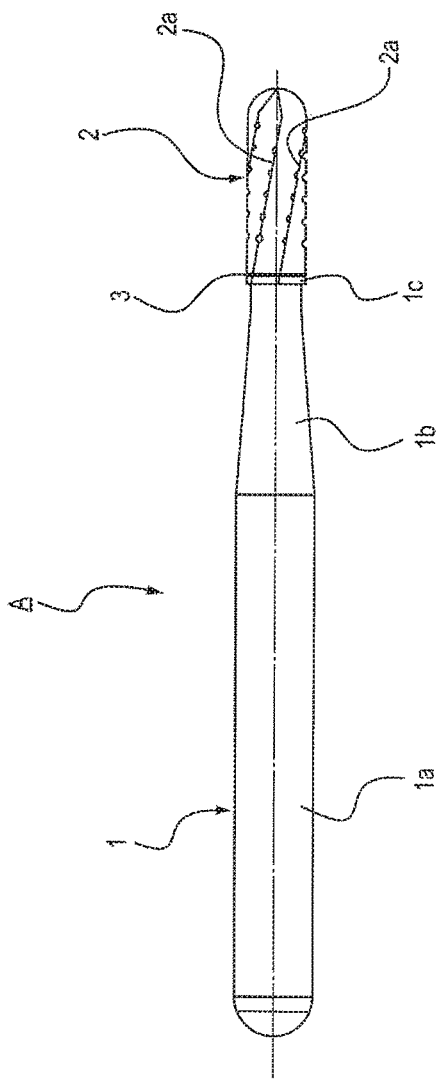
FIG. 1 is a diagram illustrating a configuration of a cutting instrument.

A Cutting instrument
1 Shank portion
1a Gripper
1b Neck portion
1c Joint
1d Brazing surface
2 Working portion
2a Cutting blade
2b Brazing surface
3 Brazing portion
5a Apex
5b Sloped surface
6 Solder
7 Material
8 Intermediate material

DESCRIPTION OF EMBODIMENTS

Hereinafter, a medical cutting instrument (hereinafter, referred to as a "cutting instrument") of the invention will be described. The cutting instrument of the invention is fixed to a chuck of a handpiece gripped and operated by a hand of a doctor to be rotated, so that a working portion presses a surface layer of a tooth or a surface of a bone including an alveolar bone to cut the surface layer or the surface. In particular, a favorable cutting performance is ensured by forming the working portion using cemented carbide or ceramic, and a high durability is exhibited by forming a shank portion using stainless steel or tool steel.

In the cutting instrument of the invention, the shank portion is formed in a round bar shape made from stainless steel or tool steel, and a brazing surface is formed at an edge. Precipitation hardening stainless steel, martensitic stainless steel, or austenitic stainless steel may be employed as stainless steel forming the shank portion, and tool steel such as carbon tool steels, high-speed tool steel, or alloy tool steel may be selectively employed as the tool steel.

In addition, the working portion is made from cemented carbide or ceramic, and a brazing surface is formed at an edge. Tungsten carbide (WC) or titanium carbide used as a cutting tool in machine processing may be employed as cemented carbide forming the working portion, and carbide ceramics represented by cermet may be employed as ceramic.

A function of a protrusion portion provided on one or both of the brazing surface of the shank portion and the brazing surface of the working portion is to set a gap between the brazing surface of the shank portion and the brazing surface of the working portion, and to maintain the gap during a brazing operation. A gap between the brazing surfaces can be maintained by causing the protrusion portion provided on the brazing surface to come into contact with the opposing brazing surface. Accordingly, a brazing operation may be performed while the gap between the brazing surfaces is stably maintained, and a strength variation resulting from the brazing operation can be excluded.

As the protrusion portion provided on the brazing surface, it is only required that the protrusion portion exhibit the above functions. The shape thereof is not particularly limited. The protrusion portion may have a curved surface shape, a circular cone shape, a pyramid shape, and may have any shape including these shapes.

However, given a condition of easiness and the like of processing with respect to a material forming the shank portion or the working portion, it is preferable that the protrusion portion be formed in a sloped surface having an apex. It is also preferable that brazing be performed in a state in which the apex of the sloped surface forming the protrusion portion provided on the brazing surface is brought into contact with a flat surface or a sloped surface including an apex that forms a protrusion portion provided on another opposing brazing surface.

As described above, the protrusion portion provided on the brazing surface corresponds to one or both of the brazing surface of the shank portion and the brazing surface of the working portion. In particular, when the protrusion portion is provided on the brazing surface of one of the shank portion and the working portion, it is preferable that the protrusion portion be provided on the brazing surface of the shank portion since the shank portion is formed using stainless steel or tool steel having an excellent workability. It is preferable that the brazing surface be formed at an edge of the shank portion in a longitudinal direction (axial direction).

The sloped surface having the apex provided on the brazing surface is brazed in a state in which the sloped surface comes into contact with the flat surface or the sloped surface including an apex of the opposing brazing surface. That is, the height of the sloped surface defines a gap between two opposing brazing surfaces, and sets a capacity of solder in the brazing portion. Thus, it is preferable that the height of the sloped surface be changed in response to the thickness in the joint portion between the shank portion and the working portion.

In an experiment of the inventors, it is preferable that the height of the sloped surface provided on the brazing surface be set in the range of 0.5% to 8% of the diameter of the brazing surface. When the height is less than a value in the range, an amount of solder is small, and thus it is difficult to obtain a sufficient joint strength. In addition, when the height is greater than a value in the range, an amount of solder is large, and thus workability deteriorates, cost increases, and variation occurs in a joint strength. In particular, to obtain a uniform and sufficiently great joint strength, it is preferable that the height of the sloped surface provided on the brazing surface be set in the range of 1% to 5% of the diameter of the brazing surface.

The shank portion and the working portion are bonded to each other through the brazing portion. A material of solder used when forming the brazing portion is not particularly limited. However, a silver solder that melts at a relatively low temperature is preferable. In addition, a property of the silver solder is not particularly limited, and any of a foil shape, a bar shape, and a paste shape may be used. However, it is preferable that the cutting instrument be in a paste state since the thickness of the working portion is about 1 mm, which is thin.

Figure 2:
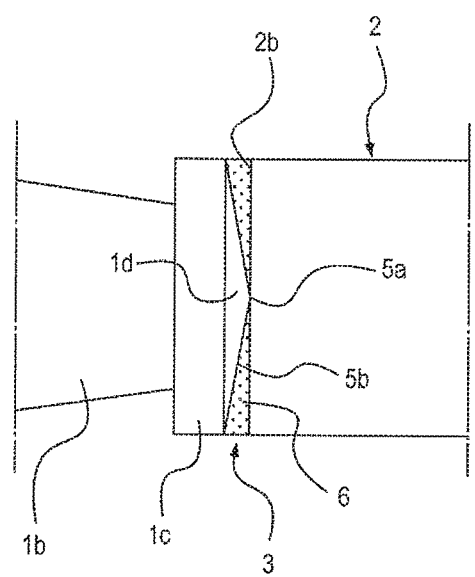
FIG. 2 is an enlarged view illustrating a configuration of a brazing portion.

Next, a configuration of the cutting instrument according to the embodiment will be described in detail with reference to FIGS. 1 and 2.

Referring to the drawings, a cutting instrument A includes a shank portion 1 fixed to a chuck of a handpiece (not illustrated), and a working portion 2 that cuts a surface layer of a tooth (not illustrated). In the embodiment, the shank portion 1 is made from austenitic stainless steel, and the working portion 2 is made from WC. The cutting instrument A is constructed when the shank portion 1 and the working portion 2 are connected and integrated with each other through the brazing portion 3 using brazing.

A specification such as an external shape, a thickness, and a length of the working portion 2 in the cutting instrument A is set according to a therapeutic purpose of a portion or a degree to be cut. Thus, the cutting instrument A illustrated in FIG. 1 is merely an example of the cutting instrument A. For example, a shape of the working portion 2 includes a round bar shape illustrated in FIG. 1 in which a leading end has a spherical shape and a thickness is uniform, a taper shape in which a leading end has a spherical shape and a thickness becomes thinner toward the leading end, a sphere shape, and the like. A plurality of spiral-shaped cutting blades 2a is formed on an outer circumference surface of the working portion 2.

In addition, a brazing surface 2b is formed on an edge face of the working portion 2 at a side of the shank portion 1. In particular, as illustrated in FIG. 2, in the embodiment, the brazing surface 2b of the working portion 2 is formed as a flat surface.

The shank portion 1 is rotated and operated while being fixed to the chuck of the handpiece. Accordingly, a gripper 1a fixed to the chuck is formed at one side of the shank portion 1. The gripper 1a has a uniform thickness corresponding to a size of the chuck regardless of a shape, a thickness, and a length of the working portion 2.

In addition, a neck portion 1b having a taper shape is formed continuously from the gripper 1a in the shank portion 1, and a joint 1c is formed at a leading end of the neck portion 1b. A brazing surface 1d is formed on an edge face of the joint 1c, and a sloped surface 5b having an apex 5a is formed on the brazing surface 1d.

As described above, the thickness of the working portion 2 is appropriately set according to a specification. Accordingly, when the diameter of the thinnest portion of the neck portion 1b is set according to the thickness of the working portion 2, types of the shank portion 1 increase. Thus, by forming the joint 1c at the leading end of the neck portion 1b, types of the shank portion 1 are decreased to attempt a reduction of stock quantity.

The joint 1c has the same diameter as an external diameter of the working portion 2, and a portion of the cutting blades 2a is continuously formed on an outer circumference surface of the joint 1c. Thus, the joint 1c is formed to have a diameter greater than the thickness of the thinnest portion of the neck portion 1b forming the shank portion 1.

The sloped surface 5b having the apex 5a formed on the brazing surface 1d of the shank portion 1 is formed as a sloped surface having a circular cone shape for an easiness of processing. By forming the sloped surface 5b in a circular cone shape, the brazing surface 1d may be fabricated concurrently with a fabrication of another portion, for example, the neck portion 1b and the joint 1c when the shank portion 1 is rotated and cut from a material having a round bar shape, which is advantageous.

In the embodiment, in a case of the cutting instrument A in which the thickness of the working portion 2 is 1.2 mm, the height of the sloped surface 5b is 0.038 mm, and is set to be about 3.1% of the thickness of the working portion 2. In addition, in a case of the cutting instrument A in which the thickness of the working portion 2 is 1.0 mm, the height of the sloped surfaced 5b is 0.031 mm, and is set to be about 3.1% of the thickness of the working portion 2. Further, in a case of the cutting instrument A in which the thickness of the working portion 2 is 0.8 mm, the height of the sloped surfaced 5b is 0.022 mm, and is set to be about 2.8% of the thickness of the working portion 2.

Herein, a bending strength in a case where a thickness of the working portion 2 is 1.0 mm, and a height of the sloped surface 5b is varied will be described.

The inventors conducted a bending test using a method defined in JIS T 5502:2001 (dental rotary instrument—test method) 3.3 neck region strength test by setting a thickness of the working portion 2 to 1.0 mm, forming the brazing surface 2b in a flat surface, providing the sloped surface 5b on the brazing surface 1d of the shank portion 1, setting a height of the brazing surface to eight types in a range from 0.003 mm to 0.09 mm, and fabricating ten test pieces for each set sizes. A bending strength desired for the cutting instrument A that cuts a hard layer such as a tooth and an alveolar bone is greater than or equal to 35 N (Newton).

Test 1, a height of the brazing surface: 0.003 mm, a ratio with respect to a thickness of the working portion 2: 0.30% (hereinafter the same applies), a bending strength was 29 N as a result of a bending test of ten tests (hereinafter the same applies). The bending strength is determined to be practically insufficient.

Test 2, a height of the brazing surface: 0.005 mm, a ratio with respect to a thickness of the working portion 2: 0.50%, a bending strength was 35 N. The bending strength is determined to be practically sufficient.

Test 3, a height of the brazing surface: 0.02 mm, a ratio with respect to a thickness of the working portion 2: 2.00%, a bending strength was 41 N. The bending strength is determined to be practically sufficient.

Test 4, a height of the brazing surface: 0.03 mm, a ratio with respect to a thickness of the working portion 2: 3.00%, a bending strength was 45 N. The bending strength is determined to be practically sufficient.

Test 5, a height of the brazing surface: 0.04 mm, a ratio with respect to a thickness of the working portion 2: 4.00%, a bending strength was 42 N. The bending strength is determined to be practically sufficient.

Test 6, a height of the brazing surface: 0.06 mm, a ratio with respect to a thickness of the working portion 2: 6.00%, a bending strength was 38 N. The bending strength is determined to be practically sufficient.

Test 7, a height of the brazing surface: 0.08 mm, a ratio with respect to a thickness of the working portion 2: 8.00%, a bending strength was 36 N. The bending strength is determined to be practically sufficient.

Test 8, a height of the brazing surface: 0.09 mm, a ratio with respect to a thickness of the working portion 2: 9.00%, a bending strength was 27 N. The bending strength is determined to be practically insufficient.

As a result of Tests 1 through 8 described above, a height at which the most favorable bending strength may be exhibited is present, and a bending strength is degraded when the height as an apex is decreased or increased. A bending strength is practically insufficient when the height is extremely low or extremely high. That is, a graph of the test result is a quadratic curve in which a ratio is 3.00% and a bending strength 45 N is an apex.

Accordingly, a range in which a practical bending strength may be exhibited is a range of 0.5% to 8% of the diameter of the brazing surface. In particular, it is more preferable that a ratio with respect to a diameter of the brazing surface be in a range of 1% to 5%, which indicates that a bending strength is in a range exceeding about 40 N.

In the brazing portion 3, the apex 5a of the sloped surface 5b provided on the brazing surface 1d of the shank portion 1 comes into contact with a flat surface of the brazing surface 2b of the working portion 2, and thus a void having a gap corresponding to a height of the sloped surface 5b is formed between the two brazing surfaces 1d and 2b. Through a solder 6 filled in the void, the shank portion 1 and the working portion 2 are bonded to each other in an integrated manner.

A solder used when the shank portion 1 and the working portion 2 are brazed is not particularly limited. However, a silver solder that melts at a relatively low temperature is preferable. In addition, a property of a solder used when a brazing operation is performed may be a foil shape and a bar shape, and is preferably a paste shape.

Since the cutting instrument A constructed as described above is gripped by the handpiece and rotates at a high speed to cut a desired portion, the working portion 2 is likely to eccentrically rotate and fracture when a center of rotation of the shank portion 1 does not accurately match a center of rotation of the working portion 2.

Figure 3:
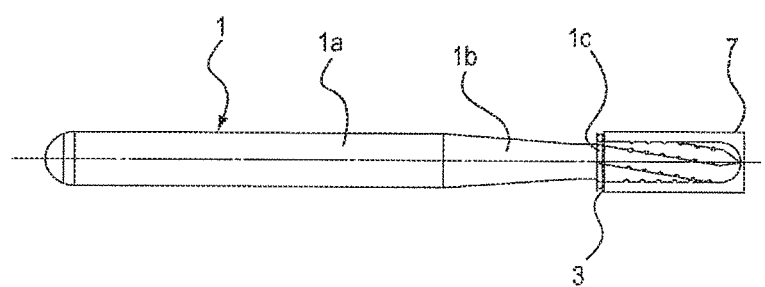
FIG. 3 is a diagram illustrating a process order when the cutting instrument is manufactured.
Figure 3:
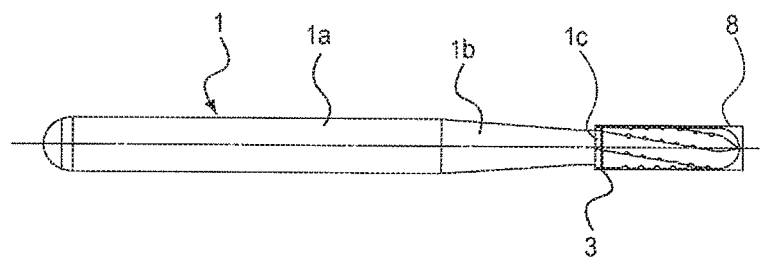
Figure 3:
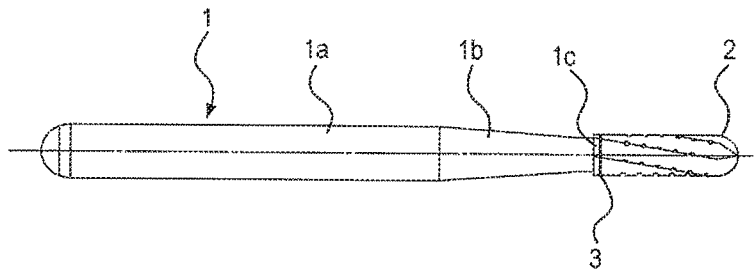

For this reason, the cutting instrument A according to the embodiment is manufactured as illustrated in FIG. 3. That is, instead of brazing cemented carbide, as the working portion 2 in which the cutting blades 2a are formed in advance, to the shank portion 1, cemented carbide sufficiently greater than a thickness and a length of the desired working portion 2 is brazed to the shank portion 1, and then the cemented carbide is processed, thereby manufacturing the cutting instrument A in which centers of rotation match each other.

First, as illustrated in FIG. 3A, a material 7 of cemented carbide sufficiently greater than a thickness and a length of the desired working portion 2 is caused to face the brazing surface 1d formed on the joint 1c of the shank portion 1. In this instance, a surface of the material 7, facing the brazing surface 1d of the shank portion 1 is the brazing surface 2b of the working portion 2, and thus is formed as a flat surface.

Thereafter, the apex of the sloped surface 5b provided on the brazing surface 1d of the shank portion 1 comes into contact with the brazing surface 2b formed on the edge face of the material 7 to construct the brazing portion 3. While maintaining the state, the solder 6 is filled between the both brazing surfaces 1d and 2b, and the brazing portion 3 is heated. The solder 6 is melted by heating the brazing portion 3, the melted solder reliably penetrates into a center section by capillary phenomenon occurring between the sloped surface 5b and the flat surface, and a void is not formed.

When the brazing portion 3 is heated for a predetermined time, and the brazing portion 3 is cooled down, the solder is solidified due to the cooling, and the shank portion 1 and the material 7 for forming the working portion 2 are brazed and integrated. In this instance, a center of rotation of the shank portion 1 may not match a center of rotation of the material 7.

Next, as illustrated in FIG. 3B, the material 7 is processed to construct an intermediate material 8. This operation is fixing the gripper 1a of the shank portion 1 to a processing equipment (not illustrated), and grinding the material 7 so that the working portion 2 has a desired thickness while causing a rotation in this state. As described in the foregoing, since a center of rotation of the gripper 1a of the shank portion 1 is a center of rotation of the cutting instrument A, a center of rotation of the intermediate material 8 accurately matches a center of rotation of the shank portion 1 even when a center of rotation of the material 7 does not match the center of rotation of the shank portion 1.

Next, as illustrated in FIG. 3C, the intermediate material 8 is processed to form a hemispherical edge, and the spiral-shaped cutting blades 2a are formed on a circumference surface. Through the processing, the working portion 2 is formed of the material 7 through the intermediate material 8, thereby manufacturing the cutting instrument A.

INDUSTRIAL APPLICABILITY

In the cutting instrument of the invention, the working portion 2 is formed of cemented carbide which is extremely hard, and thus it is advantageous to use the cutting instrument when cutting a hard portion including a bone in a general surgery, not being limited to a hard surface layer of a tooth, an alveolar bone, or a dental treatment.

The invention claimed is:

1. A method of producing a medical cutting instrument, the medical cutting instrument including a shank portion which has a first brazing surface and is formed of a round stainless steel bar or a round tool steel bar and a working portion which has a second brazing surface and is formed of cemented carbide or ceramic at a leading end of the shank portion, the first brazing surface being a conical surface with a single apex and the second brazing surface being a flat surface, the method comprising the steps of:
   a) placing a material and the shank portion such that the first brazing surface is opposed to the second brazing surface which is a surface of the material, and that the first brazing surface is in contact with the second brazing surface only at the single apex;
   b) connecting the material with the shank portion using solder such that the solder is placed in a space provided between the first brazing surface and the second brazing surface with the first brazing surface being opposed to the second brazing surface and the first brazing surface being in contact with the second brazing surface only at the single apex;
   c) processing the material while rotating the shank portion around the center axis of the shank portion to produce an intermediate member such that the center axis of the shank portion corresponds to the center axis of the intermediate member even when the center axis of the shank portion does not correspond to the center axis of the material; and
   d) forming a blade on the intermediate member, and wherein the working portion is formed of the material through the intermediate member to produce the medical cutting instrument including the shank portion and the working portion.

2. The method of producing a medical cutting instrument according to claim 1, further comprising the step of:
   a) forming a hemispherical shape at an end of the intermediate member before forming the blade on the intermediate member.

* * * * *